United States Patent [19]

Noda et al.

[11] 4,024,223

[45] May 17, 1977

[54] STRIPE COMPOSITION AND METHOD OF REDUCING SMELL ASSOCIATED THEREWITH

[75] Inventors: Kanji Noda, Chikushino; Kazuki Furuya; Satoru Miyata, both of Tosu; Toyoaki Yoneda, Fuchu, all of Japan

[73] Assignees: Teijin Limited, Osaka; Hisamitsu Pharmaceutical Co., Inc., Saga, both of Japan

[22] Filed: Apr. 22, 1975

[21] Appl. No.: 570,429

Related U.S. Application Data

[63] Continuation of Ser. No. 413,253, Nov. 6, 1973, abandoned.

[30] Foreign Application Priority Data

Nov. 11, 1972  Japan .......................... 47-112593

[52] U.S. Cl. .............................. 424/180; 424/235; 424/343
[51] Int. Cl.$^2$ ....................................... A61K 31/70

[58] Field of Search ........... 424/180, 235, 145, 148

[56] References Cited

UNITED STATES PATENTS 2,137,169  11/1938  Levey ............................... 424/230

OTHER PUBLICATIONS

Chemical Abstracts, vol. 72 (1970), p. 59028e.
Chemical Abstracts, vol. 66 (1967), p. 32418w.

*Primary Examiner*—V. D. Turner
*Attorney, Agent, or Firm*—Sherman & Shalloway

[57] ABSTRACT

A stupe composition comprising a stupe base and an antiphlogistic and analgetic medicine, said medicine containing an interacted compound selected from the group consisting of an interacted compound of menthol and a cyclodextrin and an interacted compound of methyl salicylate and a cyclodextrin. The said composition is prepared by uniformly mixing a stupe base and the interacted compound.

2 Claims, No Drawings

STRIPE COMPOSITION AND METHOD OF REDUCING SMELL ASSOCIATED THEREWITH

This is a continuation of Application Ser. No. 413,253, filed Nov. 6, 1973, now abandoned.

This invention relates to a stupe composition having reduced discomfortable or stinging smell inherent to the conventional stupe compositions for external application and giving a wet packing effect for prolonged periods of time, and to a process for preparing said composition.

Generally, various cases, such as pains from blow, sprain, tumescence, myosalgia, lumbago, contusion, stiff shoulder, neuralgia, rheumatism, arthritis, bronchites, tonsillities, mastitis, mastodynia, toothache, parotitis, perfringeration, headache, and catarrhal pharyngitis, can be treated with stupe compositions. The stupe compositions are applied to the surface of the skin, and clothings such as stockings or underwear come into contact with the applied compositions. In the case of toothache, the composition is naturally used near the nose. Consequently, the odor of the medicament is transferred to the clothings, or the odor stimulates the olfaction excessively. Thus, the use of the stupe composition causes discomfort, and sometimes, it is not rare that the smell causes side-effects such as headache or nausea. Furthermore, the users of the stupe compositions now available contain antiphlogistic and analgetic medicines may sometimes cause discomfort to other people present near them.

It has therefore been desired to provide a stupe composition having no or reduced discomfortable or stinging smell without affecting the pharmaceutical effect of the composition.

No such stupe compositions have ever been prepared in the art. Prior attempts made in the art include a method wherein an odorless antiphlogistic and analgetic drug is blended, or a method wherein the pharmaceutically effective ingredients are masked by a perfume having a stronger smell than these ingredients. However, all of these known methods have the defect that sufficient stuping effects cannot be obtained, or the use of masking perfume caused skin irritation. Moreover, the smell of the masking perfume is not pleasing equally to all the users, and it has been impossible to provide a masked stupe which smells pleasing to everybody.

It is extremely difficult to remove the odor of the currently available stupes without causing a reduction in pharmaceutical effect, while using antiphologistic and analgetic drugs now in use.

A further requirement of the stupe composition is that the pharmaceutical effect must be maintained for prolonged periods of time. Conventional stupe compositions are a mere paste-like mixture of kaolin, glycerol, water and volatile stupe medicines, and therefore, the water and the medicines in the compositions volatilize in several hours, simultaneously, causing the loss of the pharmaceutical effect. Only a minor part of the medicines is absorbed from the skin, and the greater part of them tends to dissipate by the influences of the outer atmosphere, the body temperature and the humidity and cannot be utilized effectively.

Extensive studies have been made in order to remove the offensive smell of the stupe composition and to maintain the effect of the composition for prolonged periods of time. As a result, we have found that the discomfortable or stinging smell of the conventional stupe composition is ascribable mainly to menthol and methyl salicylate contained in it; an interacted compound (or molecular compound) of menthol and a cyclodextrin and an interacted compound of methyl salicylate and a cyclodextrin can be prepared; and that by using the above interacted compounds instead of the menthol and methyl salicylate previously used for antiphologistic and analgetic drugs for stupe compositions, the discomfortable and stinging smells are extremely reduced, and a stupe composition for external application having markedly improved suitability for use can be provided.

Accordingly, an object of this invention is to provide a stupe composition having markedly reduced discomfortable or stinging smell and improved suitability for use and exhibiting a wet packing effect for prolonged periods of time.

Many other objects of this invention along with its advantages will become more apparent from the following description.

The cyclodextrin itself to be used for preparing the active ingredient used in this invention is a known compound which may often be called cycloamylose or Schardinger dextrin. The cyclodextrin may, for example, be a substance which is commonly used as a column filler in gas-chromatography or a carrier for medicines. It has a structure wherein the glucose molecules are bonded cyclically, and usually consists of about 6 to 8 glucose molecules. The method for its preparation is well known, and it can be prepared, for example, by the method disclosed at page 281 of "Die Stärke", 15, Nr. 8 (1963 which involves causing cyclodextrin glycosyltransferase to act on starch or a hydrolyzed product of starch thereby to decompose and cleave the helical structure of the starch and bond the cut ends.

The cyclodextrin can also be prepared by the method disclosed in Japenese Patent Publication No. 2380/71 which compises causing amylase of *Bacillus macerans* to act on starch that has been lightly liquified to a DE of not more than 15.

The cyclodextrin so prepared is available for example, as α-cyclodextrix (cyclohexamylose), β-cyclodextrin (cycloheptaamylose), and γ-cyclodextrin (cyclooctamylose). Usually, it is obtained as a mixture of these cyclodextrins. If desired, the individual components of the mixture can be separated and purified by for example fractional precipitation. In the present invention, these cyclodextrins are used either as a mixture or as separated indivudual components. From the viewpoint of availability and cost, the use of β-cyclodextrin is preferred.

The interacted compound of menthol and/or methyl salicylate with a cyclodextrin can be prepared by bringing menthol and/or methyl salicylate into intimate contact with at least one cyclodextrin in the presence of water. The water may be bonded or added water which these menthol, methyl salicylate and the cyclodextrin may contain, but usually, water is positively added to the reaction system.

For example, 10 to 20 parts by weight of menthol and/or methyl salicylate, 90 to 150 parts of cyclodextrin and 20 to 60 parts by weight of water are sufficiently kneaded by a kneader. When the viscosity of the mixture increases, a small amount of water may further be added. Then, the kneaded mixture is added to about 5 times its volume of water, and the precipitate formed is collected by filtration and dried to form a powdery product. The suitable temperature at the time of kneading is about 5° to 7° C., especially preferably about 15° to 30° C. Usually, the kneading is performed for about 30 minutes to about 4 hours.

Another method of preparing the interacted product comprises adding menthol and/or methyl salicylate to an aqueous solution of a cyclodextrin, stirring the mixture for 30 minutes to 4 hours, and allowing the mixture to stand for 3 to 6 hours, followed by filtering and drying. The suitable stirring temperature is about 5° to 70° C., preferably about 30 to about 50° C. The preferred temperature for standing the stirred mixture is room temperature or lower.

The interacted compound used as an active ingredient of the stupe composition of this invention has properties evidently different from those of a mere mixture of menthol and/or methyl salicylate with a cyclodextrin. We assume that this interacted compound is in the form of an inclusion compound consisting of the menthol and/or methyl salicylate as a guest compound and the cyclodextrin as a host crystal.

Even when the interacted compound is extracted by means of a Soxhlet extractor for 24 hours, not all of the menthol or methyl salicylate is extracted out. For example, when an interacted compound containing 11.6% by weight of menthol based on the weight of β-cyclodextrin with ether for 24 hours, 11.0% by weight of the menthol still remains in the interacted compound, and no further extraction of the menthol can be carried out. Furthermore, when an interacted compound containing 9.0% by weight of methyl salicylate based on β-cyclodextrin is extracted with ether for 24 hours using a Soxhlet extractor, 8.6% by weight of the methyl salicylate still remains in the interacted compound, and the methyl salicylate is not extracted further.

It has not been made clear yet in what form the extracted menthol or methyl salicylate is included, connected, or merely adhered in the rings of the cyclodextrin and/or among the rings of the cyclodextrin. However, in view of the fact that when a mere mixture of menthol and β-cyclodextrin or a mere mixture of methyl salicylate and β-cyclodextrin is extracted with ether under the same conditions, substantially all of the menthol or methyl salicylate is extracted, it is clear that some interaction has occured between the menthol or methyl salicylate and the cylodextrin in the stupe composition of this invention. Furthermore, it was observed that an endothermic peak by differential thermal analysis appears at about 95° C. in the case of an interacted compound of menthol and cyclodextrin and at about 88° C. in the case of an interacted compound of methyl salicylate and cyclodextrin, while no such endothermic peak is observed with cyclodextrin, menthol, methyl salicylate, a mixture of cyclodextrin and menthol, and a mixture of cyclodextrin and methyl salicylate. Thus, we assume that the interacted compound of this invention is probably an inclusion compound consisting of the menthol and/or methyl salicylate as a guest compound and the cyclodextrin as a host crystal.

It has been confirmed that in the interacted compound used in this invention, the proportion of the menthol or methyl salicylate can vary over a range of 5 to 15% by weight based on the weight of the cyclodextrin.

When a mere mixture of menthol and a cyclodextrin, and interacted compound of menthol and cyclodextrin, and an interacted compound of methyl salicylate and cyclodextrin were evaluated by a panel of experts for detection of smell, the panel reported that no reduction in detectable smell was observed in the case of the mere mixtures, but that in the interacted compounds, the inherent smell of the menthol or methyl salicylate substantially disappeared. From this fact also, the interacted compounds used in this invention are clearly distinguished from the mere mixtures.

Since the interacted compound can be prepared by bringing menthol and/or methyl salicylate into intimate contact with a cyclodextrin in the presence of water, it is not necessary to prepare the interacted compound in advance and then mix it with a stup base, but it is possible to form the interacted compound at the time of formulating the stupe composition. Accordingly, we refer in the present specfication to the uniform mixing of an interacted compound of menthol and a cyclodextrin or an interacted compound of methyl salicylate and a cyclodextrin with a stupe base, not only does it mean the embodiment of using the above interacted compound, but also it refers to the instance where menthol and/or methyl salicylate and a cyclodextrin are uniformly mixed with other components under the conditions for forming an interacted compound.

Various conventional stupe bases can be suitably selected and incorporated in the stupe composition of this invention. Examples of the base are kaolin, bentonite, talc, wax, petrolatum, sodium lactate, zinc oxide, boric acid, and aluminum silicate. They can be used either alone or in combination with each other. The stupe composition of this invention may further contain other drugs, a tackifier, a softener, or a mositure retaining agent.

Examples of the other drugs are glycol salicylate, salicylic acid, peppermint oil camphor, thymol, creosote, taurine, scopolia extract, diphenhyramine hydrochloride, diphenhydramine, mercurochrome, phellodedron ustum, plum extract, zanthoxylum oil, borneol, and meprylcaine. They may be used either alone or in combination with each other. Examples of the tackifier include sodium alginate methyl cellulose, a carboxyvinyl polymer, carboxymethyl cellulose, ethyl cellulose, polyvinylpyrrolidone, polyvinyl alcohol, polyvinyl methyl ether, tragacanth rubber, atactic polypropylene, guaiacol, ester gum, natural rubber latex, and gelatin. The softeners may be liqud paraffins and silicone. The moisture retaining agent may, for example, be glycerol, propylene glycol, polyethylene glycol, diethyl glycol monoethyl ether, magnesium oxide, sorbitol, urea, or aluninun acetate.

Where peppermint oil, thymol, camphor, creosote, borneol, or other compound having a stinging odor is incorporated as the other medicine, it is preferred that they are also incorporated in the form of an interacted compound with a cyclodextrin, same as in the case of menthol and methyl salicylate.

Several preferred embodiments of preparing the stupe composition of this invention are shown below.

1. Method wherein an antiphlogistic and analgetic drug, a stupe base and water are placed in a stirrer together with a cyclodextrin, and the mixture is stirred until the entire mixture becomes paste-like.

2. Method comprising adding an antiphlogistic and analgetic drug to a suitable amount of a cyclodextrin, and stirring the mixture to form an interacted compound, and kneading this compound together with a stupe base and water with stirring.

3. Method comprising forming an aqueous solution of a cyclodextrin, adding an antiphlogistic and analgetic drug to the aqueous solution, stirring the mixture throughly, allowing the stirred mixture to stand, collecting the precipitated interacted compound by filtration, followed by drying and pulverizing the product, placing the resulting powdery interacted compound in a stirrer together with a stupe base and water, and stirring the mixture until the entire mixture becomes paste-like.

The kneaded mixture so obtained is made into a final product by placing it in a suitable receptacle, or by coating it on a suitable backing and then covering the coated surface with a strippable liner. The backing may, for example, be a cloth, non-woven cloth, paper, or synthetic resin sheet. The backing may be stretchable in at least one of the longitudinal and transverse directions. The liners may, for example, be cellophane, or a plastic film such as a polyethylene film. If desired, a releasing agent may be coated on the liner for the ease of stripping off.

The amount of the interacted compound to be used in the composition of this invention is not critical, but usually, it is 10 to 95% by weight, preferably 20 to 40% by weight, based on the weight of the composition.

The following Examples illustrate the preparation of the stupe composition in accordance with this invention. All parts in the Examples are those by weight.

EXAMPLE 1

40 parts of β-cyclodextrin and 55 parts of water were placed in a kneader equipped with a stirrer and held at 20° to 30° C., and stirred for 40 minutes to make the mixture paste-like. To the paste-like mixture was added 5 parts of a mixture of 24 parts of methyl salicylate, 24 parts of menthol, 36 parts of peppermint oil, 14 parts of camphor and 2 parts of thymol, and the mixture was kneaded with stirring for 2 hours to form an interacted compound. Then, 30 parts of the above mixture containing the interacted compound of methyl salicylate and menthol with the cyclodextrin, 15 parts of kaolin, 7 parts of polyvinyl alcohol, 10 parts of gelatin, 20 parts of propylene glycol and 18 parts of water were sufficiently kneaded for 15 minutes in a high speed stirring-type kneader held at 60° to 100° C.

The paste-like mixture so obtained was coated uniformly on a flannel sheet in a thickness of about 2 mm. The coated surface was covered with a polyethylene film.

In use, the polyethylene film was stripped off, and the flannel sheet was adhered to the affected part. There was hardly any smell inherent to the stupe during treatment. The moisture retaining effect was considerably superior to the conventional stupe compositions. Specific data about the effect will be shown below. A control example was one in which a kneaded mixture of the same composition as in Example 1 was used instead of using a mere mixture (conventional stupe) using the same amount of kaolin instead of β-cyclodextrin.

[Test Method]

1. Smell

A functional test was conducted by a panel of 15 experts (consisting of 10 men and five women) with an age of 18 to 25. The test results were evaluated on a scale of +++ which shows a very strong odor, ++ which shows a strong odor, + which shows a slight odor, and − which shows no odor.

2. Moisture retaining effect

This was determined by a rate of weight decrease and a functional test.

a. Rate of weight decrease

The sample used was paste-like mixture containing 17.0% by weight of water and 3.0% by weight of a volatile drug mixture consisting of l-menthol, camphor, mehtyl salicylate and thymol. A piece having an area of about 100 cm$^2$ was cut out from the sample, and the released paper was removed. It was then allowed to stand in a constant temperature-humidity chamber held at 24.8° C. and a humidity of 50% with the paste-containing side facing upward. The sample was rapidly weighed every predetermined period of time, and weight change was measured. Then, the weight decrease at the end of each specified period of time was divided by the weight of the paste-like mixture previously determined, thereby to determine the rate of weight decrease of the paste-like mixture per unit weight.

The weight of the paste-like mixture was determined as follows:

A piece having a predetermined area was cut out from the sample, and its entire weight was measured. The paste part was then washed off with warm water and an organic solvent such as ether or alcohol, followed by drying. The weight of the backing cloth was measured, and subtracted from the weight of the entire cut sample.

b. Functional test

Four samples each having an area of about 100 cm$^2$ were adhered to the left and right backs of 15 males ranging from 18 to 52 in age in substantially symmetrical relation. (Four samples of the Example using the stupe composition of this invention were adhered to one back, and four control samples containing no cyclodextrin, to the other back). One sample in each of the group of samples in accordance with the present invention and the group of control samples was removed at the end of each of 4, 8, 12 and 24 hours. The mositure retention of each of the samples so removed was evaluated by an expert using a sense of touch.

The results obtained by the above tests were as follows:

Table 1

Results of the Functional Tests of Smell

| Examples | degree of Smell | Source of Smell Methyl salicylate | Menthol |
| --- | --- | --- | --- |
| Example | +++ | 0 persons | 0 persons |
|  | ++ | .0 | 0 |
|  | + | 3 | 0 |
|  | − | 12 | 15 |
| Control | +++ | 8 | 7 |
|  | ++ | 7 | 7 |
|  | + | 0 | 1 |
|  | − | 0 | 0 |

Table 2

| Examples | Time that elapsed (hours) | Rate of weight decrease (5) | | | | | | | |
|---|---|---|---|---|---|---|---|---|---|
| | | 1 | 2 | 3 | 4 | 5 | 6 | 7 | 8 |
| Example | | 3.95 | 6.37 | 7.92 | 9.60 | 10.77 | 11.18 | 11.34 | 11.40 |
| Control | | 4.16 | 6.87 | 8.61 | 10.78 | 12.37 | 13.95 | 14.73 | 14.95 |

The results in each of the Example and Control are an average of four replicates. The weight of the paste-like mixture was 10.6560 g/99.8 cm² cloth in the Example, and 10.6191 g/99.5 cm² cloth in the Control.

Table 3

| Results of the Functional tests of moisture retention | | | | |
|---|---|---|---|---|
| Period of application (hours) | 4 | 8 | 12 | 24 |
| Example | 15 persons | 12 | 10 | 8 |
| Control | 15 | 7 | 3 | 0 |

The number in Table 3 shows the number of test samples which the expert judged have mositure retention.

It is clear from the above results that the stupe composition of this invention has hardly any odor, and has remarkably good moisture retention.

EXAMPE 2

1.5 parts of an antiphlogistic and analgetic drug composed of 24% of methyl salicylate, 24% of menthol, 36% of peppermint oil, 14% of camphor and 2% of thymol, 18.5 parts of β-cyclodextrin, 8 parts of bentonite, 30 parts of kaolin, 35 parts of water, and 7 parts of propylene glycol were placed in a stirrer, and stirred for 30 minutes to form an interacted compound. When, the mixture became paste-like, it was withdrawn from the stirrer and filled in a bottle.

In use, a suitable amount of the paste-like mixture was taken out, and coated on a cloth. It was applied to the affected part and supported by an adhesive tape. During treatment, there was detected hardly any odor inherent to the stupe composition, and it had superior mositure retaining effect. The functional test results were almost the same as those in Example 1.

EXAMPLE 3

3.0 parts of β-cyclodextrin and 96.7 parts of water were placed in a stirrer, and stirred to form an aqueous solution. To the solution was added 0.3 part of an antiphlogistic and analgetic drug consisting of 24% of methyl salicylate, 24% of menthol, 36% of peppermint oil, 14% of camphor and 2% of thymol, and the mixture was stirred for 4 hours. The stirred mixture was allowed to stand for about 12 hours, and the precipitate was collected by filtration with a filter paper. The collected precipitate was allowed to dry in air for 24 hours to form a powdery interacted compound. Then, 40 parts of the above powder containing the interacted compound, 12 parts of kaolin, 6 parts of polyvinyl alcohol, 8 parts of gelatin, 18 parts of propylene glycol, and 16 parts of water were kneaded sufficiently with stirring for 30 minutes by means of a high speed stirrer held at 60° to 100° C.

The resulting paste-like mixture was coated on a flannel sheet in a thickness of about 2 mm, and the coated surface of flannel sheet was covered with a polyethylene film.

In use, the polyethylene film was stripped off, and it was applied to the affected part. During treatment there was no odor inherent to the stupe composition, and the moisture retaining time was prolonged as compared with the conventional stupe compositions. The functional test results were much the same as those obtained in Example 1.

What we claim is:

1. A method for reducing the discomfortable or stinging smell of a stupe composition and improving a wet packing effect of the same which comprises mixing 10 to 95% by weight, based on the weight of the composition, of an inclusion compound selected from the group consisting of an inclusion compound of menthol and β-cyclodextrin and an inclusion compound of methyl salicylate and β-cyclodextrin with a stupe base selected from the group consisting of kaoline, bentonite, talc, wax, sodium lactate, zinc oxide, boric acid, and aluminum silicate.

2. The method as defined in claim 1 wherein the amount of menthol or methyl salicylate in said inclusion compound is 5 to 15% by weight, based on the weight of said β-cyclodextrin.

* * * * *

UNITED STATES PATENT OFFICE
CERTIFICATE OF CORRECTION

Patent No. 4,024,223               Dated May 17, 1977

Inventor(s) NODA, ET AL.

It is certified that error appears in the above-identified patent and that said Letters Patent are hereby corrected as shown below:

Claim 1, line 10, after "wax," insert -- petrolatum, --

Signed and Sealed this sixteenth Day of August 1977

[SEAL]

Attest:

RUTH C. MASON
*Attesting Officer*

C. MARSHALL DANN
*Commissioner of Patents and Trademarks*